United States Patent [19]

Katz et al.

[11] Patent Number: 5,032,123

[45] Date of Patent: Jul. 16, 1991

[54] LASER CATHETER WITH RADIALLY DIVERGENT TREATMENT BEAM

[75] Inventors: Bob H. Katz, Plantation; Kent Wreder, Miami, both of Fla.

[73] Assignee: Cordis Corporation, Miami Lakes, Fla.

[21] Appl. No.: 458,097

[22] Filed: Dec. 28, 1989

[51] Int. Cl.$^5$ .............................................. A61B 17/32
[52] U.S. Cl. .................................... 606/15; 128/398
[58] Field of Search .................................. 606/13–16; 128/395–398

[56] References Cited

U.S. PATENT DOCUMENTS

| | | | |
|---|---|---|---|
| 4,233,493 | 11/1980 | Nath | 128/398 |
| 4,266,548 | 5/1981 | Davi | 350/358 |
| 4,341,873 | 7/1982 | Robinson et al. | 350/96.34 |
| 4,343,638 | 8/1982 | Mitachi et al. | 65/2 |
| 4,449,532 | 5/1984 | Storz | 128/20 |
| 4,559,942 | 12/1985 | Eisenberg | 128/395 |
| 4,583,526 | 4/1986 | Ali | 128/6 |
| 4,583,539 | 4/1986 | Karlin et al. | 128/395 |
| 4,616,901 | 10/1986 | MacChesney et al. | 350/96.34 |
| 4,648,892 | 3/1987 | Kittrell et al. | 128/398 |
| 4,681,104 | 7/1987 | Edelman | 128/398 |
| 4,784,132 | 11/1988 | Fox et al. | 128/303.1 |
| 4,819,632 | 4/1989 | Davies | 128/398 |
| 4,834,093 | 5/1989 | Littleford et al. | 606/16 |
| 4,854,315 | 8/1989 | Stack et al. | 128/398 |

FOREIGN PATENT DOCUMENTS

| | | |
|---|---|---|
| 0214712A1 | 3/1987 | European Pat. Off. |
| 5583011 | 12/1978 | Japan |
| 60104903 | 11/1983 | Japan |
| 2071500 | 9/1981 | United Kingdom |

OTHER PUBLICATIONS

Cothren et al., "A Multifiber Catheter with an Optical Shield for Laser Angiosurgery", *Lasers in the Life Science*, 1 (1), Jan. 1986, pp. 1–12.

Lammer, MD et al., "Contact Probes for Intravascular Laser Recanalization", *Invest Radiology*, vol. 24, pp. 190–195, Aug. 1988.

*Primary Examiner*—Max Hindenburg
*Attorney, Agent, or Firm*—Watts, Hoffman, Fisher & Heinke Co.

[57] ABSTRACT

A laser catheter having a flexible body and a distally positioned translucent end cap coupled to the flexible body by a metal coupler. Multiple fiber optic light pipes extend through the body and direct light through the end cap at oblique angles. The light passing through the catheter originates from a visible light pulsed dye laser.

18 Claims, 2 Drawing Sheets

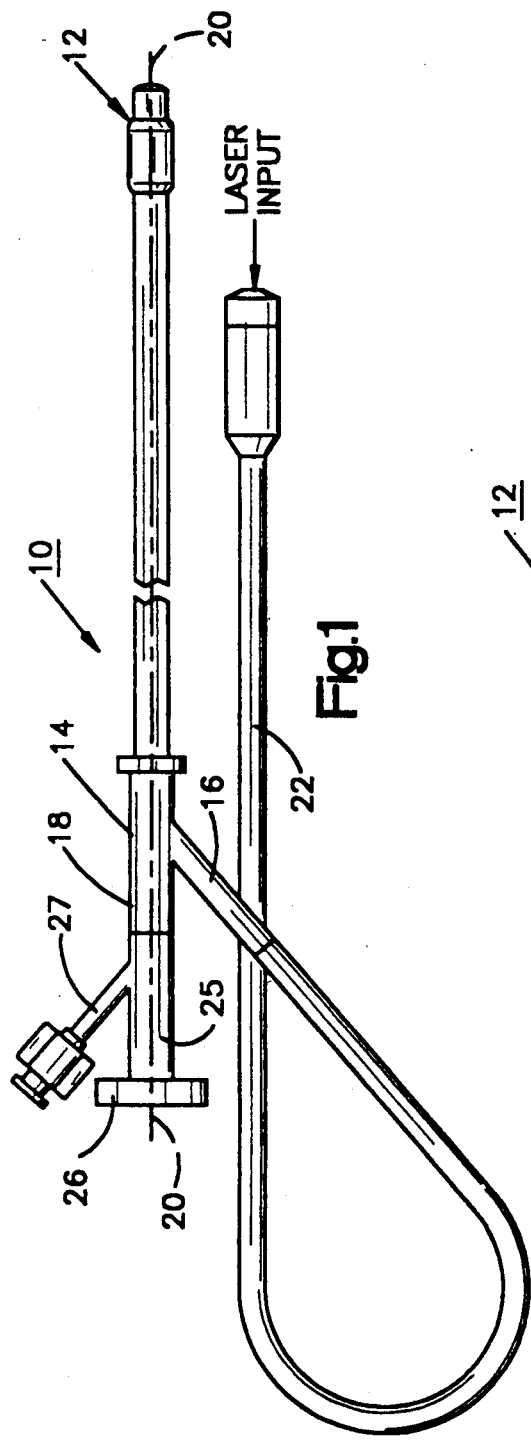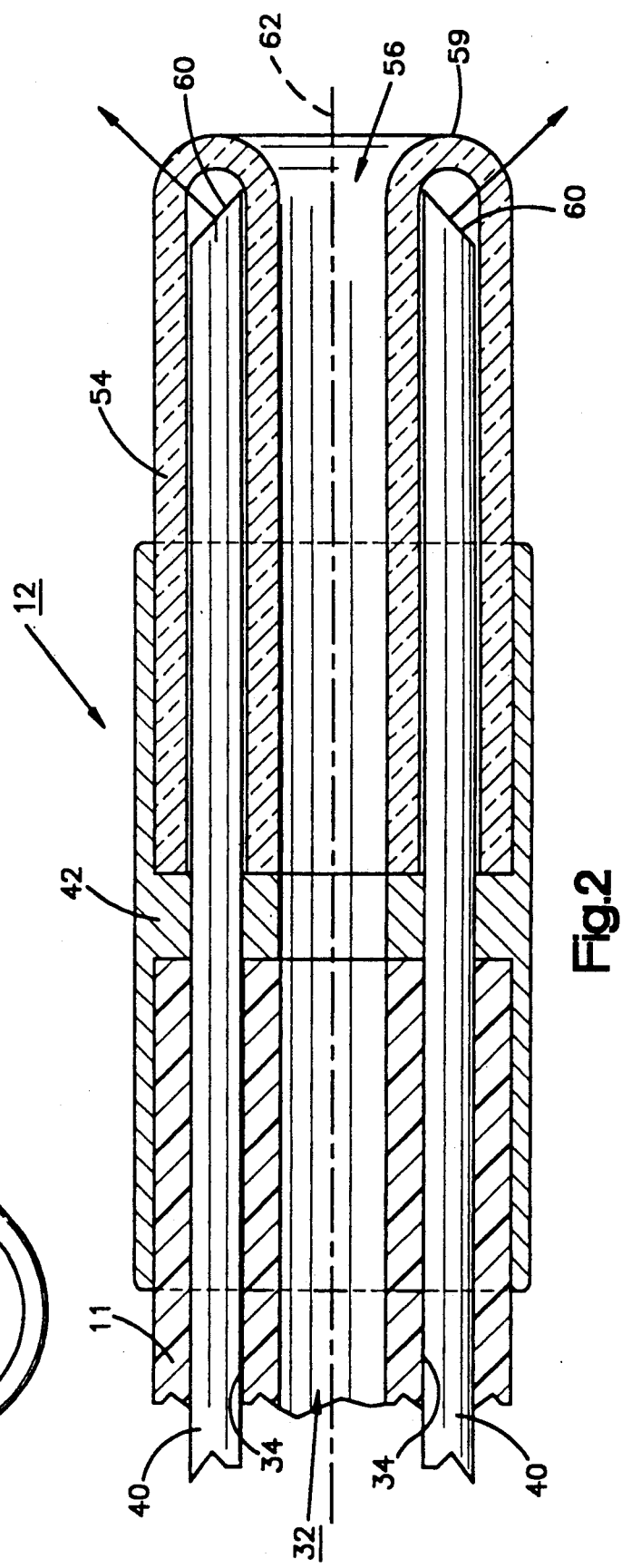

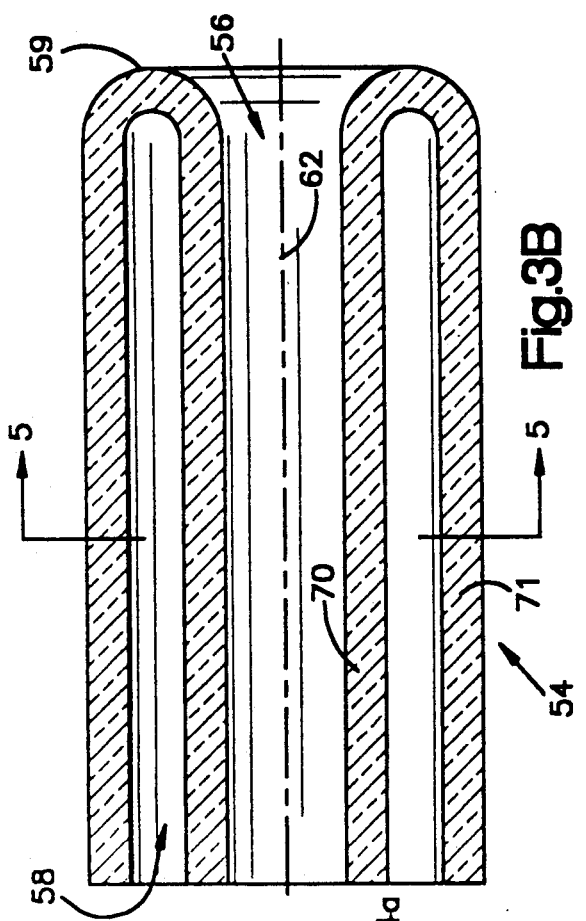
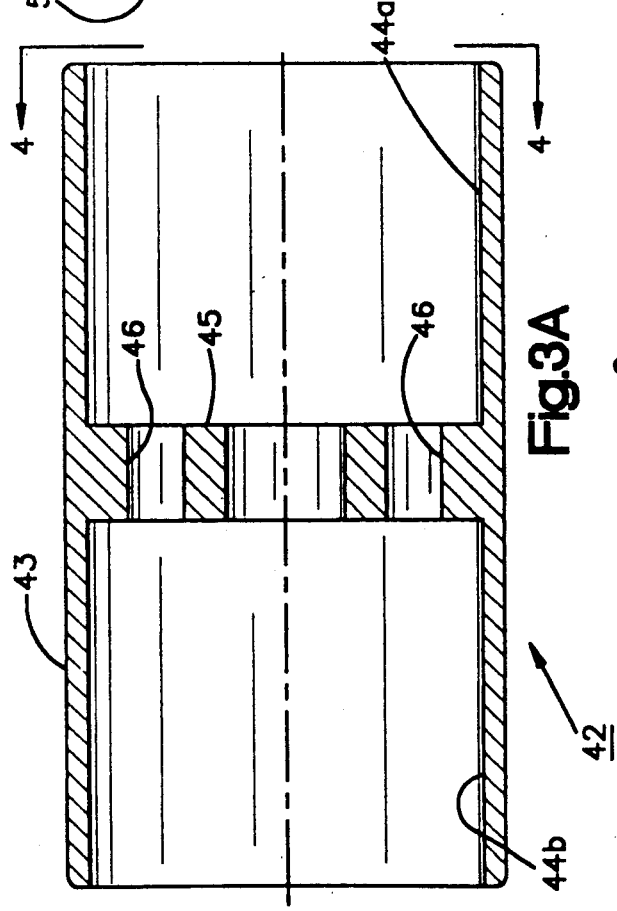
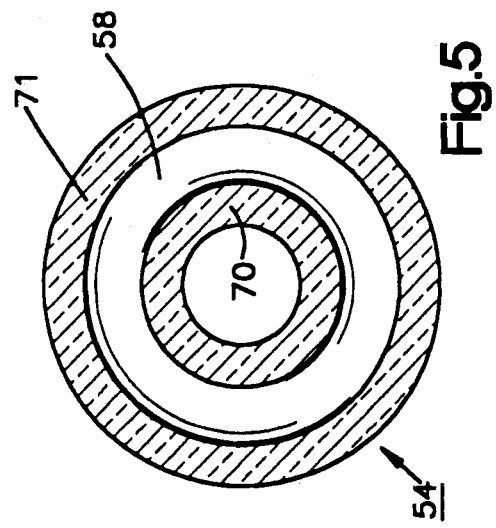
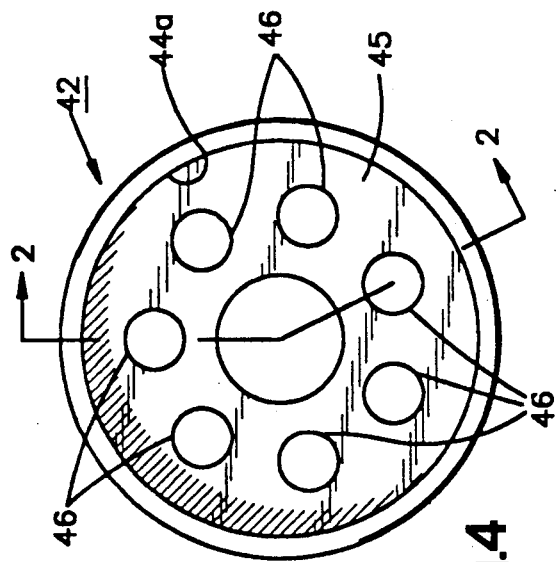

LASER CATHETER WITH RADIALLY DIVERGENT TREATMENT BEAM

FIELD OF THE INVENTION

The present invention concerns a catheter for delivering light energy to a target region of a subject vessel to dislodge material from the vessel. A preferred use of the invention is for removing deposits from the inner wall linings of a blood vessel.

BACKGROUND ART

Prior art proposals for laser removal of unwanted deposits or diseased tissue from inner wall linings of a blood vessel are known. These techniques are generically referred to as percutaneous transluminal laser angioplasty (PTLA). The use of laser catheters for treatment of carotid and coronary artery stenoses have been proposed and preliminary tests that have been conducted suggest these devices can effectively increase blood flow through partially or totally blocked blood vessels.

A printed publication to Cothren, et al. entitled "A Multi Fiber Catheter with an Optical Shield for Laser Angiosurgery," *Lasers in the Life Sciences* 1(1), 1986, 1–12, documents a proposed catheter system having multiple optical fibers. The optical fibers extend the length of a laser catheter and direct light at the catheter's distal end through an optical shield. The system proposed in this publication includes 19 optical fibers arranged to include a center fiber, an inner ring of 6 fibers, and an outer ring of 12 fibers. The excitation or firing sequence of the fibers is controlled by a computer. The goal of each firing sequence is to produce a hole within diseased arterial tissue. The firing sequence is conducted and the laser catheter tip can be inserted further into the hole before a next firing sequence conducted.

The article to Lammer, et al. entitled "Contact Probes for Intravascular Laser Recanalization" in *Radiology*, 1989, 24. discloses a laser catheter having a single optical light pipe which terminates at a distal end of the catheter and is covered by a sapphire tip which concentrates or focuses the excitation light delivered through the fiber optic light pipe to a focused region in close proximity to the sapphire tip. Some light scattering occurs at the entry and exit boundaries of the sapphire tip so that as noted in this publication "circumferential energy distribution also occurs."

U.S. Pat. No. 4,854,315 to Stack, et al. concerns a laser catheter having multiple light pipes which extend through a catheter body to deliver light energy to the distal tip of the catheter. The multiple light pipes are spaced around a center axis of the catheter and terminate in proximity to a window which conducts the light from the multiple light pipes to the vessel being treated.

DISCLOSURE OF THE INVENTION

The present invention concerns a laser catheter having multiple light pipes for delivering light energy to a distal end of the laser catheter. These light pipes are configured to direct the light energy outwardly against vessel walls rather than directing light energy to a point or region closely adjacent the distal end of the catheter.

In accordance with the preferred embodiment of the invention, the catheter includes an elongated flexible body having a central axial throughpassage to accommodate a guide wire, for example. Multiple axially eccentric throughpassages are spaced radially outward from the center throughpassageway about a catheter body. Multiple fiber optic light pipes are positioned within the eccentric throughpassages and extend beyond a distal end of the flexible body. A translucent cap defines an enclosed space for covering distal ends of light pipes. The translucent cap also defines a central opening that extends the passageway for the guidewire.

In accordance with a preferred design, the end surfaces of the light pipes are machined to define normal angles at approximately 45° with respect to the elongated axis of the catheter. When so configured, the light transmitted through the fiber optic light pipes is emitted from the light pipes and strikes inner wall linings of the vessel and ablates undesirable plaque from the inner wall. This causes light energy to strike the material which is to be removed from the vessel wall but not the material lying directly in front of the catheter tip. This configuration of the light pipes eliminates the need for targeting of the catheter tip and centering of the catheter within the vessel. The fibers of the catheter can be activated individually or in combination to direct energy against specific regions of the vessel wall.

Other features and advantages associated with practice of the invention are disclosed in the accompanying detailed description of the preferred embodiment of the invention which is described in conjunction with the accompanying drawings.

BRIEF DESCRIPTION OF THE DRAWINGS

FIG. 1 is a side view of a laser catheter for treating a region of a vessel by irradiating an inner wall of the vessel;

FIG. 2 is an enlarged partially sectioned view of a distal end of the laser catheter depicted in FIG. 1;

FIG. 3A is a section view of a metal coupler and FIG. 3B is a section view of a transparent end cap which encloses a distal end of fiber optic light pipes that extend through the catheter;

FIG. 4 is an end view of the metal coupler shown in FIG. 3; and

FIG. 5 is a section view of the transparent end cap.

DETAILED DESCRIPTION OF THE DRAWINGS

FIG. 1 depicts an elongated catheter 10 having a flexible body 11 which can be positioned within a subject. A distal end 12 of the catheter 10 directs fiber optic transmitted light energy originating from a laser outside the subject to a treatment region. The preferred use of the catheter 10 is for removing deposits from the inner wall linings of a blood vessel.

At a proximal end of the catheter 10 a bifurcating adaptor 14 includes a side branch 16 and in line branch 18. The side branch 16 defines throughpassages for fiber optic light pipes (FIG. 2) and the in line branch has a passageway for a guide wire 20 which can be used to help position the catheter 10 within the subject.

Attached to the side branch 16 of the bifurcating adaptor 14 is a light conveying attachment 22. The attachment 22 has a bundle of fiber optic light pipes that convey light energy from a source such as a laser to the adaptor 14 and into the catheter 10.

A second bifurcating adapter 25 includes a manipulator 26 at the proximal end of the catheter 10 that is used for orienting the catheter 10 within the subject. An attending physician uses the manipulator 26 both during insertion of the catheter as well as during light energy treatment of the subject. The second adapter 25 includes an in-line branch to accommodate the guidewire 20 and a side branch 27 that includes a Leur fitting to allow fluid to be introduced into or withdrawn from a center passageway which extends to a distal end of the catheter.

A sectioned view of the distal end 22 of the catheter 10 (FIG. 2) shows a center passageway 32 for the guidewire 20 and also depicts a plurality of through passages 34 located radially outside the center passageway 32 for accommodating multiple individual fiber optic light pipes 40 which extend the length of the catheter from the bifurcating adaptor 14 into the subject. A variety of suitable materials such as plasticized vinyl resins, polyethylene, synthetic and natural rubbers and polyurethane elastomers can be used to fabricate the catheter body 11. A preferred catheter body 11 is constructed of nylon. The flexible fiber optic light pipes 40 pass through the passageways 34 and extend beyond the distal end of the flexible body 11.

A metal collar 42 having a generally cylindrical outer surface 43 is attached to a distal end of the flexible body 11. Extending into the collar 42 from both ends are openings 44a, 44b bounded by relatively thin walled segments of the metal collar 42. A center wall section 45 defines throughpassages 46 to accommodate passage of the fiber optic light pipes 40 through the collar 42. The metal collar is radio-opaque and therefore is readily visible on x-ray viewing equipment used by the physician to monitor progress of the catheter 10 as it is inserted into the subject.

The collar 42 supports an end cap 54 constructed from a translucent material and into which the ends of the flexible fiber optic light pipes 40 extend. The end cap 54 is preferably constructed from quartz.

As seen in the sectioned view of FIG. 3, the end cap 54 defines a through passage 56 to accommodate the guide wire 20 and additionally defines an annular region 58 closed at one end to accommodate receipt of the multiple fiber optic light pipes 40 carried by the flexible catheter body 11. A blunt end portion 59 of the end cap 54 forms the extreme distal end of the catheter 10 which reduces the likelihood of traumatic contact between the catheter 10 and the inner lining of a blood vessel.

The extreme distal end of each light pipe 40 is ground or polished to define a end face 60 having a normal surface angled at 45° with respect to the axial direction of the light pipe. This polished end face directs light energy travelling through the catheter away from the light pipe at an angle roughly 45° to a central axis 62 defined by the catheter 10 at its distal end. The light pipes extend into the end cap 54 a sufficient distance such that the light pipe end surface 60 is in close proximity to the curved enclosed end portion of the end cap 54 so that light exiting the fiber optic light pipe 40 passes outwardly through the end portion 59 at a generally normal or perpendicular angle and therefore little refraction occurs as the light exits through the end cap 54. The quartz end cap 54 diffuses the light energy emanating from the light pipe to reduce the concentration of light energy to avoid damaging vessel walls.

The laser used to activate the individual light pipes of the catheter 10 is a visible light (480 nm) pulsed dye laser. A suitable pulsed dye laser is commercially available from Candela Laser Company of Wayland, Mass. The fiber material chosen for the fiber optic light pipes is fused silica. The diameter of each fiber is 0.2 mm.

The flexible catheter body 11 is fabricated using an extrusion technique wherein the nylon material is extruded through a mold. The throughpassages in the flexible body 11 for accommodating the fiber optic light pipes 40 are formed by jets or streams of air forced into the mold during the extrusion process. Subsequent to fabrication of the flexible body 11, individual fiber optic light pipes can be pushed through the body from the proximal to distal end and beyond.

The metal collar 42 stabilizes the distal end of the light pipes in a desired orientation. More particularly, each of the light pipes is arranged such that the distal end 60 of the light pipe has an end face directed obliquely at a 45° angle with respect to the center axis 62. The collar 42 holds the light pipe in this orientation.

The annular cavity 58 is approximately 0.25 mm wide. The 0.20 mm diameter light pipes are inserted into the cavity 58 of the end cap and the end cap easily slide over the distal end of the light pipes until they mates with the metal collar 42. A medical grade epoxy adhesive is used to bond the end cap and the metal coupler 42 to secure the end cap in place.

The center passageway 56, 32 of the end cap and flexible body respectively has a dimension of approximately 0.97 mm or 0.038 inches. The diameter of the catheter 10 is approximately 0.097 inches or 2.46 mm.

The end cap 54 is constructed using two quartz tubes 70, 71 that are appropriately dimensioned prior to fabrication. The inner diameter of a smaller tube defines the throughpassage 46 of the completed end cap and therefore has an inner diameter of approximately 0.038 inches. The spacing between the outer diameter of the inner tube 70 and the inner diameter of the outer tube defines the cavity 58 into which the distal ends of the light pipes extend. The two tubes are cut to length and then the blunt end surface 49 formed by fusing one end of the tubes together and polishing or grinding this end to form the blunt end surface 59.

The present invention has been described with a degree of particularity. It is the intent, however, that the invention include all modifications and alterations from the disclosed design falling within the spirit or scope of the appended claims.

We claim:

1. A catheter for treating a subject vessel with light energy comprising:

(a) an elongated flexible body having a length sufficient to extend into a subject to a treatment region within the vessel and defining a first axial throughpassage extending through the elongated flexible body from a proximal to a distal end for accommodating a catheter guide wire; said flexible body further defining a plurality of additional axial passageways extending through the elongated flexible body;

(b) a plurality of light-conducting fibers positioned in the additional axial through passages, each light-conducting fiber having a light emitting end portion projecting out of a distal end of the elongated flexible body terminating in an end face; said end face being polished to an angle to direct light perpendicularly away form the end face and obliquely away from a central axis of the body toward a wall of the subject vessel; and (c) an end cap attached to the flexible body to isolate the lightconducting fibers form the subject vessel having a curved light transmissive portion for transmitting without refraction obliquely directed light emanating from the end face of the light conducting fibers to the subject vessel wall.

2. The apparatus of claim 1 wherein each fiber end face defines a normal angle perpendicular to the end face that forms an angle of substantially 45° with the central axis of the body.

3. The apparatus of claim 1 wherein the plurality of light-conducting fibers are positioned symmetrically about the first axial throughpassage within the body.

4. The apparatus of claim 1 wherein the end cap comprises a hollow translucent cap encapsulating the end portion of the light-conducting fibers, said cap having a central opening communicating with the first throughpassage in the body.

5. The apparatus of claim 4 wherein the cap is composed of quartz.

6. The apparatus of claim 4 wherein an exposed surface of the cap is blunt.

7. A catheter comprising:
   (a) an elongated flexible body having an axial central throughpassage and multiple eccentric throughpassages spaced radially outward from the central throughpassage;
   (b) multiple fiber optic light pipes positioned in said eccentric throughpassages and extending beyond a distal end of the elongated flexible body;
   (c) a translucent cap defining an enclosed space and a central opening; and
   (d) a rigid collar having a proximal opening for receiving a distal end portion of the body, a distal opening for receiving a proximal end portion of the translucent cap, a central channel communicating with said proximal and distal openings for connecting the central throughpassage of the body with the central opening of the cap, and a plurality of eccentric channels for connecting the eccentric throughpassages of the body with the enclosed space of the cap.

8. An apparatus according to claim 7 wherein the rigid collar is composed of metal.

9. An apparatus according to claim 7 wherein the rigid collar is radiopaque.

10. An apparatus according to claim 7 wherein the proximal end portion of the cap has an outer diameter no greater than an inner diameter of the distal opening of the collar and wherein the proximal end portion of the cap terminates in a shoulder having an outer diameter no less than an outer diameter of the collar for abutment with a distal end of the collar.

11. The apparatus of claim 7 wherein the cap is composed of quartz.

12. The apparatus of claim 7 wherein an exposed surface of the cap is blunt.

13. The apparatus of claim 7 including an eccentric guy wire positioned in the eccentric throughpassage for controllably deflecting a distal portion of the apparatus.

14. The apparatus of claim 7 wherein the lightconducting fiber has an end portion projecting out of a distal end of the eccentric throughpassage into the enclosed space of the cap, said end portion terminating in a face directed
   (a) obliquely from a central axis of the body; and
   (b) parallel to or at an angle no less than a critical angle of the light-conducting fibre from an outward normal directed from the central axis of the body through a central axis of the light-conducting fibre.

15. The apparatus of claim 14 wherein the critical angle of the light-conducting fibre is greater than 45. and the face is directed at an angle of substantially 45° from the central axis of the body.

16. The apparatus of claim 14 wherein the face is directed radially outward from a central axis of the body.

17. A catheter comprising:
   (a) an elongated flexible body having an axial central through passage;
   (b) multiple fiber optic light pipes carried by the body and extending beyond a distal end of the elongated flexible body;
   (c) a translucent cap defining an enclosed space and a central opening; and
   (d) a rigid collar having a proximal opening for receiving a distal end portion of the body, a distal opening for receiving a proximal end portion of the translucent cap, a central channel for connecting the central through passage of the body with the central opening of the cap, and a plurality of eccentric channels for connecting the light pipes with the enclosed space of the cap.

18. A catheter for treating a subject vessel with light energy comprising:
   (a) an elongated flexible body having a length sufficient to extend into a subject to a treatment region within the vessel and defining a first axial throughpassage extending through the elongated flexible body from a proximal to a distal end for accommodating a catheter guide wire; said flexible body further defining a plurality of additional axial passageways extending through the elongated flexible;
   (b) a plurality of light-conducting fibers positioned in the additional axial throughpassages, each light-conducting fiber having a light emitting end portion projecting out of a distal end of the elongated flexible body terminating in an end face; said end faces configured to emit light beams perpendicularly away from the end face and obliquely away from a central axis of the body toward a wall of the subject vessel such that each light beam diverges from the other light beams; and
   (c) an end cap attached to the flexible body to isolate the lightconducting fibers from the subject vessel having a curved end portion for transmitting without refraction obliquely directed light emanating from the end face of the light conducting fibers to the subject vessel wall.

* * * * *